United States Patent [19]
Drake

[11] 3,962,337
[45] June 8, 1976

[54] HYDROGENATION OF UNSATURATED DINITRILES EMPLOYING PALLADIUM AND RUTHENIUM CATALYST IN AQUEOUS TERTIARY ALKANOL

[75] Inventor: Charles A. Drake, Bartlesville, Okla.

[73] Assignee: Phillips Petroleum Company, Bartlesville, Okla.

[22] Filed: Oct. 29, 1974

[21] Appl. No.: 518,747

[52] U.S. Cl............................ 260/583 K; 252/430; 252/472; 260/583 P
[51] Int. Cl.² ......................................... C07C 87/14
[58] Field of Search...................... 260/583 K, 583 P

[56] References Cited
UNITED STATES PATENTS

| | | | |
|---|---|---|---|
| 2,640,082 | 5/1953 | Schreyer | 260/583 K |
| 2,690,456 | 9/1954 | Renfrew et al. | 260/538 K |
| 3,117,162 | 1/1964 | Rylander et al. | 260/583 K |
| 3,177,258 | 4/1965 | Rylander et al. | 260/583 K |
| 3,350,439 | 10/1967 | Feldman et al. | 260/583 K |
| 3,372,195 | 3/1968 | Little | 260/583 K |
| 3,408,397 | 10/1968 | Feldman et al. | 260/583 K |

Primary Examiner—Arthur P. Demers

[57] ABSTRACT

The cataytic hydrogenation of an olefinically unsaturated dinitrile reactant of the formula

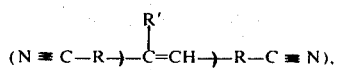

$$(N≡C-R)-\overset{R'}{\underset{|}{C}}=CH)-R-C≡N),$$

wherein each R is an alkylene or an alkylidene radical, and each R' is an alkyl radical, is carried out in the presence of $NH_3$, hydrogen, water, a tertiary alkanol, and a catalyst comprising a first component selected from the group consisting of elemental palladium, palladium compounds which are reducible by hydrogen to elemental palladium, and mixtures thereof, and a second component selected from the group consisting of elemental ruthenium, ruthenium compounds which are reducible by hydrogen to elemental ruthenium, and mixtures thereof.

20 Claims, No Drawings

HYDROGENATION OF UNSATURATED DINITRILES FOR EMPLOYING PALLADIUM AND RUTHENIUM CATALYST IN AQUEOUS TERTIARY ALKANOL

This invention relates to a process for the preparation of saturated aliphatic diamines by the catalytic hydrogenation of olefinically unsaturated aliphatic dinitriles.

In general, various processes for the catalytic hydrogenation of olefinically unsaturated aliphatic dinitriles to saturated aliphatic diamines are known to the art. Group VIII metal catalysts such as cobalt, nickel, ruthenium, rhodium, or palladium have been employed as effective catalysts for the hydrogenation of various feedstocks in these processes. However, it has been discovered that many of these hydrogenation catalyst materials are not always efficient or effective for the hydrogenation of olefinically unsaturated aliphatic dinitriles having the formula

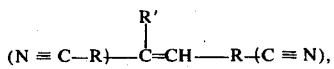

wherein each R is an alkylene or an alkylidene radical, and each R' is an alkyl radical.

In accordance with this invention, these branched-chain olefinically unsaturated aliphatic dinitriles are efficiently reduced to branched-chain saturated aliphatic diamines under suitable hydrogenation conditions in a single reaction zone by the use of a catalyst comprising a first component selected from the group consisting of elemental palladium, palladium compounds which are reducible by hydrogen to elemental palladium at the hydrogenation conditions employed and mixtures thereof, and a second component selected from the group consisting of elemental ruthenium, ruthenium compounds which are reducible by hydrogen to elemental ruthenium at the hydrogenation conditions employed and mixtures thereof; in the presence of ammonia, hydrogen, water, and at least one tertiary alkanol.

It is an object of this invention to provide a process for the catalytic hydrogenation of branched-chain olefinically unsaturated aliphatic dinitriles to branched-chain saturated aliphatic diamines. Another object is to provide an efficient one-step process for the catalytic hydrogenation of an unsaturated dinitrile having the formula

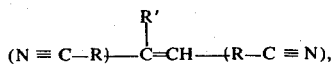

wherein each R is an alkylene or an alkylidene radical, and each R' is an alkyl radical. Still another object is to provide an efficient process for the catalytic hydrogenation of a mixture of branched-chain olefinically unsaturated aliphatic dinitriles to produce saturated aliphatic diamines in a single reaction zone. Still another object is to provide an efficient process for the catalytic hydrogenation of branched-chain olefinically unsaturated aliphatic dinitriles under reaction conditions which limit the occurrence of byproduct-forming reactions. A further object of this invention is to increase the productivity of a process for the catalytic hydrogenation of branched-chain olefinically unsaturated aliphatic dinitriles. Other objects, aspects and advantages of the invention will be apparent from a study of the specification and the appended claims.

The branched-chain unsaturated aliphatic dinitriles which are considered to be advantageously and efficiently hydrogenated in accordance with the process of this invention are the unsaturated dinitriles of the formula:

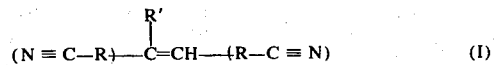

wherein each R is independently selected from the group consisting of an alkylene radical and an alkylidene radical, and R' is an alkyl radical. Each R will generally have from 1 to 15 carbon atoms, preferably from 1 to 6, and more preferably from 1 to 3 carbon atoms. R' will generally have from 1 to 15 carbon atoms, preferably from 1 to 6 carbon atoms, and more preferably from 1 to 3 carbon atoms. In general, the unsaturated dinitrile reactant of Formula (I) will contain from 7 to 30 carbon atoms, preferably from 8 to 16 carbon atoms, and more preferably from 9 to 12 carbon atoms.

Representative of unsaturated reactant species of Formula (I) include such compounds as 4-methyl-3-hexenedinitrile, 4-ethyl-3-hexenedinitrile, 5-methyl-4-nonenedinitrile, 5-ethyl-4-decenedinitrile, 7-methyl-6-tridecenedinitrile, 7-methyl-6-pentadecenedinitrile, 12-methyl-12-tetracosenedinitrile, 10-hexyl-9-tetracosenedinitrile, 2,3-dimethyl-3-hexenedinitrile, 2,4,6-trimethyl-3-heptenedinitrile, 4-ethyl-6,7-dimethyl-3-octenedinitrile, 2,4,6-triethyl-3-octenedinitrile, 2-ethyl-4,6-dipropyl-3-octenedinitrile, 2-methyl-4,6,8,10-tetrapropyl-8-dodecenedinitrile, 2,4,7,9,11,13,15-heptaethyl-6-hexadecenedinitrile, and mixtures thereof.

If desired, other olefinically unsaturated dinitrile reactants can be present and effectively hydrogenated during the hydrogenation of the unsaturated dinitriles of formula (I). Thus, in addition to the unsaturated dinitrile reactants for Formula (I), the dinitrile feed stock can contain one or more unsaturated dinitrile reactants of the formula:

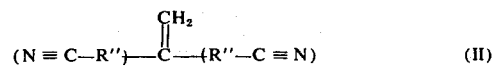

wherein each R'' is independently selected from the group consisting of an alkylene radical and an alkylidene radical. In general, each R'' will have from 1 to 15 carbon atoms, preferably from 1 to 7 carbon atoms, and more preferably from 1 to 4 carbon atoms. The dinitriles of formula (II) will generally contain from 6 to 30 carbon atoms, preferably from 8 to 16 carbon atoms, and more preferably from 9 to 12 carbon atoms. Representative unsaturated dinitrile reactants of formula (II) include such compounds as 3-methylenehexanedinitrile, 4-methyleneheptanedinitrile, 5-methylenenonanedinitrile, 6-methyleneundecanedinitrile, 7-methylenetridecanedinitrile, 8-methylenepentadecanedinitrile, 12-methylenetetracosanedinitrile, 15-methylenenonacosanedinitrile, 2-methyl-3-methylenepentanedinitrile, 2,4-dimethyl-3-methylenepentanedinitrile, 2-methyl-4-methyleneoctanedinitrile, 2-methyl-7-ethyl-4-methyleneoctanedinitrile, 2,4,8-trimethyl-6-methylenedodecanedinitrile, 2,4,8,10-tetrapropyl-6-methylenedodecanedinitrile, 2,26-dimethyl-14-methyleneheptacosanedinitrile, and mixtures thereof.

Unsaturated dinitriles having a structure other than that of formulas (I) and (II) can be present during the hydrogenation reaction, if desired. Similarly, other compounds which may be found in the feed source of the dinitriles of formulas (I) and (II) can be present so long as such additional compounds do not significantly adversely affect the hydrogenation of the dinitriles of formulas (I) and (II). Where other dinitriles are present in the feedstock, the dinitriles of formula (I) will generally constitute at least 0.1 weight percent of the total dinitriles. The significant advantages of the invention increase with increasing concentrations of the dinitriles of formula (I) in the feedstock. Thus, the process of the invention is even more advantageous for concentrations of the dinitriles of formula (I) in the feedstock of at least 5 weight percent. The invention is considered to be particularly advantageous for dinitrile feedstocks having a concentration of the dinitriles of formula (I) of at least 10 weight percent.

A presently preferred branched-chain olefinically unsaturated aliphatic dinitrile feedstock for employment in the practice of this invention is the dinitrile reaction product mixture obtained by the reaction of isobutylene and acrylonitrile. This dinitrile reaction product mixture generally comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. The first four named compounds in this mixture are of the type of formula (I), while the last three named compounds in this mixture are of the type of formula (II). The weight ratio of the dinitriles of formula (I) to the dinitriles of formula (II) in this mixture is generally in the range of about 10:1 to about 1:10.

In the practice of this invention, the catalytic hydrogenation of the unsaturated dinitrile reactant of formula (I) results primarily in the formation of saturated diamine reaction products having the formula:

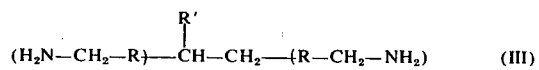

(III)

wherein R and R' are as defined hereinbefore. The catalytic hydrogenation of an unsaturated dinitrile reactant of formula (II) results primarily in the formulation of saturated diamine reaction products having the formula:

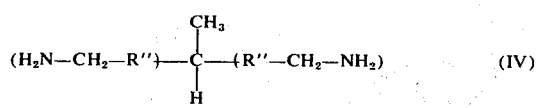

(IV)

wherein R'' is as defined hereinbefore.

The practice of this invention is particularly suited to the catalytic hydrogenation of this mixture of species of formula (I) and formula (II) for the purpose of achieving saturated diamine reaction products which are substantially free of any olefinic unsaturation and preferably essentially free of any olefinic unsaturation. The phrase "substantially free of olefinic unsaturation" signifies that the diamine reaction products contain less than about 1 weight percent olefinically unsaturated diamine reaction product based on the total weight of unsaturated and saturated diamine reaction products wherein the weight percents are determined by conventional GLC analysis. The phrase "essentially free of olefinic unsaturation" signifies that the diamine reaction products contain less than about 0.1 weight percent olefinically unsaturated diamine reaction product based on the total weight of unsaturated and saturated diamine reaction products wherein the weight percents are determined by conventional GLC analysis techniques. These diamine reaction products which are at least substantially free, and preferably essentially free, of olefinic unsaturation are advantageously employed in the preparation of linear terephthalamide polymers.

In the present hydrogenation process it appears that the nitrile groups are hydrogenated at a rate which is faster than the rate of olefinic double bond hydrogenation. Hence, when the double bond hydrogenation is complete, the nitrile group hydrogenation is also complete.

One of the most important advantages of the catalytic hydrogenation process of this invention is directly related to the production of a mixture of diamines which are essentially free of olefinic unsaturation from the olefinically unsaturated dinitrile product mixture produced by the reaction of acrylonitrile and isobutylene. This advantage is significant since prior art catalytic hydrogenation of the acrylonitrile and isobutylene reaction product mixture failed to substantially or completely reduce the olefinic unsaturation of the unsaturated dinitrile feedstock, thereby producing a reaction product mixture containing branched-chain aliphatic diamines having substantial olefinic unsaturation in the carbon skeleton. The separation of the branched-chain olefinically unsaturated diamines from the saturated diamines is inconvenient, and polyamides prepared from the mixtures containing a significant amount of unsaturated diamines have been found to be unsuited or undesirable in the preparation of polyamide fibers, particularly the terephthalamide polymers. Thus, the catalytic hydrogenation of this invention is a significant advance in the preparation of such polyamides.

The catalysts that are considered to be suitable for employment in the catalytic hydrogenation process of this invention comprise the combination of a palladium catalyst component (A) and a ruthenium catalyst component (B). The palladium catalyst component (A) can be in the form of finely divided palladium metal or compounds of palladium which are reducible by hydrogen to palladium metal at the hydrogenation reaction conditions employed. The palladium catalyst component can also be in the form of palladium metal deposited on a suitable support or in the form of hydrogen reducible compounds of palladium on a suitable support. Component (B) can be finely divided elemental ruthenium, compounds of ruthenium reducible to finely divided elemental ruthenium by hydrogen at the hydrogenation reaction conditions employed, ruthenium metal on a suitable support or hydrogen reducible compounds of ruthenium on a suitable support.

The compounds of palladium and ruthenium which are reducible by hydrogen to finely divided elemental palladium or ruthenium at the hydrogenation reaction conditions include the oxides, halides, nitrates, sulfates, oxalates, acetates, carbamates, propionates, tartrates, hydroxides, and the like, and mixtures thereof. Specific examples include palladium oxide, palladium chloride, palladium nitrate, palladium acetate, palladium carbonate, palladium hydroxide, palladium oxalate, ruthenium oxide, ruthenium chloride, ruthenium nitrate, ruthenium acetate, ruthenium carbonate, ruthenium hydroxide, and the like. The weight ratio of the ruthenium to the palladium in the mixed hydrogenation catalysts of this invention is generally in the range of about 0.1:1 to about 10:1, and preferably is in the range of about 1:1 to about 5:1.

The weight ratio of catalyst to olefinically unsaturated dinitrile reactant, based on the weight of the total of palladium and ruthenium contained therein, can be varied as desired. For the purpose of maintaining reasonable reaction rates under economically attractive catalytic reaction kinetics, it is generally preferred that the weight ratio of the total of palladium and ruthenium to the unsaturated dinitrile reactants be maintained within a range of about 0.001:100 to about 30:100, and preferably in the range of about 0.01:100 to about 5:100, and more preferably in the range of about 0.1:100 to about 0.6:100.

In the practice of this invention, it is often desirable to employ catalytic amounts of elemental palladium, elemental ruthenium, reducible compounds of palladium or ruthenium, or mixtures thereof supported by a solid catalyst carrier which does not deleteriously affect the catalytic hydrogenation process of this invention. Such supports include, for example, carbon, kieselguhr, silica, alumina, silica-alumina, calcium carbonate, barium carbonate, asbestos, pumice, clays, and the like, and mixtures thereof. The palladium and/or ruthenium catalyst components can be added to the catalyst support by any of the methods well known in the art. For example, the supported catalysts can be prepared by dry mixing the components or by impregnating the support with a solution or dispersion of palladium and/or ruthenium in elemental form or in the form of reducible compounds thereof. The supported catalyst can be pretreated with hydrogen to reduce the compounds, or such reduction can be achieved in the hydrogenation reactor. When a support is employed, the total elemental palladium and elemental ruthenium content will generally be in the range of about 0.5 to about 50 weight percent, preferably in the range of about 1 to about 10 weight percent, based on the weight of the total catalyst composition. The presently preferred catalyst component (A) is palladium on carbon with the palladium content being about 5 weight percent of the total component (A). A presently preferred second catalyst component (B) is ruthenium on alumina, the ruthenium metal content being about 5 per cent by weight, based on the total weight of the catalyst component B and the support material therefor. This presently preferred catalyst component, as well as other suitable catalyst components such as 5 weight percent ruthenium on charcoal, are available commercially.

The mixed hydrogenation catalysts of this invention can be prepared in any convenient manner. For example, the catalyst components, either supported or unsupported, can be premixed before charging to the hydrogenation reactor or they can be added to the reactor separately in any desired order. They can also be prepared by employing a single support material which is then impregnated with solutions of suitable compounds of palladium (A) or ruthenium (B) followed by hydrogen reduction to give the mixed catalyst on a single support material.

The hydrogenation reaction can be conducted at any suitable reaction conditions. In general the hydrogenation reaction will be conducted under liquid phase conditions. Any catalytic hydrogenation temperature can be employed which provides the desired degree of catalytic efficiency in the hydrogenation of the branchedchain olefinically unsaturated aliphatic dinitrile containing feedstock. The hydrogenation temperatures will generally be within the range of about 100° C to about 300° C, preferably within the range of about 160° C to about 250° C, and more preferably within the range of about 165° C to about 200° C. However, when the reaction temperature employed is in the low end of the temperature range, it is considered desirable, if not necessary to employ higher hydrogen pressures and/or longer reaction times in order to readily achieve the desired degree of hydrogenation.

The catalytic hydrogenation of branched-chain olefinically unsaturated aliphatic dinitriles can be carried out at any hydrogen pressure wherein both the olefinic unsaturation and the nitrile groups are reduced in the presence of ammonia, hydrogen and the diluent. Generally, suitable hydrogen pressures are within the range of from about 500 to about 5,000 psig, but lower or even higher hydrogen pressures can be employed. Preferably, due to economic considerations, hydrogen pressures within the range of about 750 to about 3000 psig are employed.

Any time interval suited for the catalytic hydrogenation of branched-chain olefinically unsaturated aliphatic dinitriles can be employed in the practice of this invention. However, time intervals economically attractive to the process are generally within the range of about 15 minutes to about 5 hours for a batch hydrogenation process. A reaction time in the range of about 1 to about 3 hours is presently preferred in order to insure substantially complete hydrogenation of any olefinic bonds in the feedstock as well as complete hydrogenation of the nitrile groups to primary amino groups. The catalytic hydrogenation of unsaturated dinitriles in accordance with the process of this invention can be carried out as a continuous process at any suitable liquid hourly space velocity (LHSV). However, the liquid hourly space velocity rates will generally be within the range of about 0.1 to about 10, more preferably from about 0.5 to about 2, volumes of unsaturated dinitrile reactant plus diluent per volume of catalyst (including the volume of any catalyst support if any is present).

The effects of the temperature, pressure and reaction time employed in the hydrogenation process are generally interrelated, and it is within the routine skill to determine suitable ranges for any two of these variables for a given value of the third variable.

The diluent utilized in the hydrogenation process of the present invention is a mixture of water and at least one tertiary alkanol wherein the concentration of the water in the diluent is suitable to provide the desired degree of hydrogenation under the other reaction conditions employed. In general, the water constitutes from about 5 to about 25 weight percent, preferably from about 6 to about 20 weight percent, and more preferably from 8 to 16 weight percent of the diluent mixture. Suitable alkanols include the unsubstituted tertiary aliphatic alcohols having 4 to 12 carbon atoms per molecule, and mixtures thereof. The term "unsubstituted" signifies that there are no substituents other than hydrocarbyl radicals. Examples of suitable tertiary alkanol diluents include 2-methyl-2-propanol, 2-methyl-2-butanol, 3-ethyl-3-hexanol, 2-ethyl-2-hexanol, 2,4-dimethyl-2-pentanol, 2,3-dimethyl-3-pentanol, 3-ethyl-3-pentanol, 3,7-dimethyl-3-octanol, 3-ethyl-3-decanol, and the like, and mixtures thereof. To facilitate handling of the reaction mixtures, the weight ratio of unsaturated dinitrile reactants to diluent charged to the reaction zone is generally within the weight ratio range of about 0.001:100 to about 25:100, is preferably in the range of about 0.01:100 to about 22:100, and more preferably is in the range of about 0.1:100 to about 20:100.

Ammonia is employed in the process of this invention as a means of suppressing undesirable side reactions such as the formation of secondary and tertiary amines. Any amount of ammonia can be employed which is effective in deterring or reducing undesirable side reactions. In general, the mol ratio of ammonia to cyano group (there being two cyano groups in each unsaturated dinitrile) will be in the range of about 1:1 to about 25:1, and preferably will be in the range of about 7:1 to about 15:1.

Recovery of the desired end product, the branched-chain saturated aliphatic diamines, including preferred branched-chain saturated aliphatic diamine reaction products which contain less than about 0.1 percent olefinically unsaturated diamine by weight of the total reaction product as determined by GLC (gas-liquid chromatograph analysis), as well as any resulting reaction byproducts, any unconsumed reactants, ammonia, hydrogen, and/or diluents can be carried out by any conventional separation means. In general, at the conclusion of the catalytic hydrogenation process, the reaction zone effluent is cooled and depressurized with the recovery, if desired, of any ammonia or diluent which is vented from the reaction zone effluent during the depressurization operation. The ammonia or diluent can be returned or recycled to the hydrogenation zone if desired. The reaction products can be separated from the catalyst by conventional filtration means. The filtrate containing the at least substantially completely saturated diamines can be conveniently separated from any reaction byproducts or any diluent remaining in the filtrate by any conventional fractional distillation.

The following example is presented in further illustration of the invention, but should not be unduly construed in limitation thereof.

EXAMPLE

In each of a series of runs, a one-liter autoclave was charged with an amount of the purified reaction product of two mols of acrylonitrile with one mol of isobutylene. This reaction product consisted essentially of a mixture of isomeric unsaturated dinitriles having one carbon-carbon double bond and 10 carbon atoms per molecule. The principal isomers were 5-methylene-nonane-dinitrile and 5-methyl-4-nonenedinitrile with very small amounts of more highly branched isomers such as 2-methyl-4-methylene-octanedinitrile, among others. For simplicity, the above-described reaction product will hereafter be called diadduct. A catalyst and a diluent were also charged to the one-liter autoclave. The system was then flushed with nitrogen and then charged with ammonia. The reactor was then pressured with hydrogen and heated at an elevated temperature. The mixture was stirred throughout the reaction period. After this one-step hydrogenation reaction, the reactor was cooled, vented and the contents filtered to remove the catalyst. The filtrate was distilled under vacuum to remove essentially all of the diluent. Gas-liquid chromatograph (GLC) analysis of the product was employed to determine whether the reduction of the unsaturated dinitriles was complete. The operating conditions and results are set forth in the following table:

TABLE

| Run | Catalyst[a] | Diadduct Amount gm | Diadduct[b] Concentration, Wt. % | t-Butanol Amount gm | Water Amount gm | Water[c] Concentration, Wt. % | NH$_3$ Amount gm | H$_2$ Pressure psig | Temp., °C | Reaction Time, Hours | Unsaturation,[d] % |
|---|---|---|---|---|---|---|---|---|---|---|---|
| 1 | B | 30 | 9.6 | 248 | 35 | 12.4 | 60 | 1000 | 170 | 2¼ | 10[e] |
| 2 | B | 30 | 9.8 | 276 | — | — | 60 | 1000 | 170 | 2¼ | 10[e] |
| 3 | C | 30 | 7.9 | 315 | 35 | 10 | 60 | 1200 | 170 | 2¼ | 100[f] |
| 4 | C | 30 | 7.9 | 350 | — | — | 60 | 1200 | 170 | 2¼ | 100[g] |
| 5 | A | 30 | 9.6 | 252 | 30 | 10.6 | 60 | 1000 | 170 | 2¼ | 0[h] |
| 6 | A | 45 | 13.7 | 248 | 35 | 12.4 | 90 | 1000 | 170 | 2¼ | 0[h] |
| 7 | A | 45 | 14.1 | 276 | — | — | 90 | 1000 | 170 | 2¼ | 10[i] |
| 8 | A | 50 | 19.5 | 182 | 25 | 12.1 | 100 | 1000 | 170 | 2¼ | 0[h] |
| 9 | A | 75 | 28.7 | 166 | 25 | 13.1 | 152 | 1000 | 170 | 2¼ | 80[j] |
| 10 | A | 75 | 28.2 | 166 | 25 | 13.1 | 150 | 1000 | 170 | 5 | 70[k] |
| 11 | A | 50 | 20.7 | 182 | 10 | 5.2 | 100 | 1000 | 170 | 2¼ | 75[l] |
| 12 | A | 30 | 10.0 | 250 | 20 | 7.4 | 60 | 1200 | 170 | 2¼ | 0[h] |
| 13 | A | 45 | 13.2 | 245 | 50 | 16.9 | 90 | 1200 | 170 | 2¼ | 0[h] |
| 14 | A | 50 | 17.7 | 182 | 50 | 21.5 | 100 | 1000 | 170 | 2¼ | 15[m] |
| 15 | D | 50 | 19.5 | 182 | 25 | 12.1 | 100 | 1200 | 170 | 2 | 0[h] |
| 16 | D | 50 | 19.5 | 182 | 25 | 12.1 | 100 | 1000 | 150 | 2 | 15[n] |

TABLE-continued

| Run | Catalyst[a] | Diadduct Amount gm | Diadduct[b] Concentration, Wt. % | t-Butanol Amount gm | Water Amount gm | Water[c] Concentration, Wt. % | NH₃ Amount gm | H₂ Pressure psig | Temp., °C | Reaction Time, Hours | Unsaturation,[d] % |
|---|---|---|---|---|---|---|---|---|---|---|---|
| 17 | D | 50 | 19.5 | 182 | 25 | 12.1 | 100 | 150 | 100 | 2 | 100[o] |

[a]The catalysts employed are as follows:
  A. 2 Grams of 5 percent by weight ruthenium on alumina, and 1 gram of 5 percent by weight palladium on charcoal.
  B. 5 Grams of 5 percent by weight ruthenium on alumina.
  C. 5 Grams of 5 percent by weight palladium on charcoal.
  D. 2 Grams of 5 percent by weight ruthenium on alumina, and 1 gram of 5 percent by weight palladium on alumina.
[b]Concentration of diadduct in total of diadduct and diluent system.
[c]Concentration of water in the diluent system, the balance being tertiary butanol.
[d]Olefinic double bonds in the product as a percentage of the olefinic double bonds in the reactants, determined by gas chromatographic analysis.
[e]Approximately 10 percent of the original ethylenic unsaturation.
[f]No reduction of the original ethylenic unsaturation occurred and only about 10% of the nitrile groups were reduced.
[g]No reduction of the original ethylenic unsaturation occurred and only a small amount of the nitrile groups were reduced.
[h]Complete reduction of the ethylenic unsaturation and of the nitrile groups.
[i]Approximately 10% of the original ethylenic unsaturation remained, all of which was the internal (within the chain rather than in a branch) unsaturation of the 5-methyl-4-nonenedinitrile.
[j]Approximately 80% of the original ethylenic unsaturation remained as well as a substantial amount of the nitrile groups.
[k]Approximately 70% of the original ethylenic unsaturation remained as well as approximately 30% of the nitrile groups.
[l]Approximately 75% of the original ethylenic unsaturation remained as well as approximately 25% of the nitrile groups.
[m]Approximately 15% of the original ethylenic unsaturation remained, all of which was the internal (within the chain rather than in a branch) unsaturation of the 5-methyl-4-nonenedinitrile.
[n]Approximately 15% of the product contained unsaturation.
[o]No reaction was apparent.

A comparison of runs 1, 3 and 5 shows that the use of the two-component combination catalyst achieved complete saturation in an aqueous diluent system whereas neither the one-component ruthenium catalyst nor the one-component palladium catalyst achieved complete saturation under essentially similar reaction conditions. In fact the one-component palladium catalyst did not achieve any significant reduction of the ethylenic unsaturation in run 3, and effected the reduction of only about 10% of the nitrile groups. A comparison of runs 1 and 2 demonstrates that there is no apparent improvement in the addition of water to the t-butanol diluent when using a single component ruthenium catalyst. Similarly, a comparison of runs 3 and 4 demonstrates that there is no apparent improvement in the addition of water to the t-butanol diluent when using a single component palladium catalyst. However, a comparison of runs 6 and 7 demonstrates the advantages of using an aqueous diluent system with the two-component catalyst system.

Runs 7, 11, 12, 5, 8, 6, 13 and 14 corresponding to 0%, 5.2%, 7.4%, 10.6%, 12.1%, 12.4%, 16.9%, and 21.5% water in the diluent system, show that for a nitrile concentration in the range of 9.6 to 20.7%, the lower limit for water to achieve complete saturation under the reaction conditions employed is somewhere between 5.2 and 7.4% and the corresponding upper limit for water is somewhere between 16.9 and 21.5% of the diluent system. Runs 8 and 14 demonstrate that the percent water in the diluent system is a major factor in achieving complete saturation under the reaction conditions employed.

Runs 5, 12, 6, 8 and 9, corresponding to 9.6%, 10.0%, 13.7%, 19.5% and 28.7% nitrile concentration in the liquid reaction medium, show that the upper limit for nitrile concentration for achieving complete saturation under the reaction conditions employed is between 20 and 28 percent nitrile concentration. Runs 9 and 10 show no improvement in doubling the reaction time with excessively high dinitrile concentration.

Reasonable variations and modifications are possible within the scope of the foregoing disclosure and the appended claims to the invention.

What is claimed is:

1. A process for the catalytic hydrogenation of an unsaturated dinitrile feedstock comprising at least one unsaturated dinitrile compound of the formula

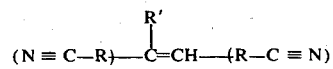

$$(N \equiv C-R)-\underset{R'}{C}=CH-(R-C \equiv N)$$

wherein each R is independently selected from the group consisting of an alkylene radical and an alkylidene radical, R' is an alkyl radical, and the number of carbon atoms in said compound is in the range of 7 to 30; which comprises contacting, at suitable hydrogenation conditions for the at least substantially complete hydrogenation of said at least one unsaturated dinitrile compound, said feedstock with ammonia; hydrogen; a diluent comprising water and at least one unsubstituted tertiary alkanol, the concentration of the water in the diluent being suitable to permit the desired degree of hydrogenation under said hydrogenation conditions; and a catalyst comprising a first catalyst component selected from the group consisting of elemental palladium and palladium compounds which are reducible by hydrogen to elemental palladium at said hydrogenation conditions, and mixtures thereof, and a second catalyst component selected from the group consisting of elemental ruthenium, ruthenium compounds which are reducible by hydrogen to elemental ruthenium at said hydrogenation conditions, and mixtures thereof, to thereby effect the at least substantially complete hydrogenation of said at least one unsaturated dinitrile compound to the corresponding branched-chain saturated aliphatic diamine.

2. A process in accordance with claim 1 wherein the water constitutes from about 5 to about 25 weight percent of said diluent.

3. A process in accordance with claim 2 wherein said suitable hydrogenation conditions comprise a weight ratio of the total of palladium and ruthenium present to the unsaturated dinitriles in the range of about 0.001:100 to about 30:100, a mol ratio of ammonia to cyano groups in the range of about 1:1 to about 25:1, a hydrogen pressure in the range of about 500 to about 5000 psig, a weight ratio of the unsaturated dinitriles to the diluent in the range of about 0.001:100 to about 25:100, a weight ratio of palladium to ruthenium in the range of about 0.1:10 to about 10:1, and a temperature in the range of about 100° C to about 300° C.

4. A process in accordance with claim 3 wherein said diluent consists essentially of water and tertiary butanol.

5. A process in accordance with claim 1 wherein the water constitutes from about 6 to about 20 weight percent of said diluent.

6. A process in accordance with claim 5 wherein said suitable hydrogenation conditions comprise a weight ratio of the total of palladium and ruthenium present to the unsaturated dinitriles in the range of about 0.01:100 to about 5:100, a mol ratio of ammonia to cyano groups in the range of about 1:1 to about 25:1, a hydrogen pressure in the range of about 500 to about 5000 psig, a weight ratio of the unsaturated dinitriles to the diluent in the range of about 0.001:100 to about 22:100, a weight ratio of palladium to ruthenium in the range of about 0.1:10 to about 10:1, and a temperature in the range of about 160° C to about 250° C.

7. A process in accordance with claim 6 wherein each of said alkylene radical, said alkylidene radical and said alkyl radical has from 1 to 15 carbon atoms, and wherein said tertiary alkanol has from 4 to 12 carbon atoms per molecule.

8. A process in accordance with claim 7 wherein said at least one unsaturated dinitrile compound comprises a mixture of 5-methyl-4-nonenedinitrile, 2,4-dimethyl-4-octenedinitrile, 2,4-dimethyl-3-octenedinitrile, and 2,4,6-trimethyl-3-heptenedinitrile.

9. A process in accordance with claim 5, wherein said feedstock further comprises at least one unsaturated dinitrile reactant of the formula

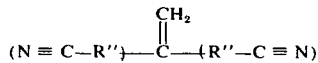

wherein each R'' is independently selected from the group consisting of an alkylene radical and an alkylidene radical, and the number of carbon atoms in said reactant is in the range of 6 to 30.

10. A process in accordance with claim 9 wherein said suitable hydrogenation conditions comprise a weight ratio of the total of palladium and ruthenium present to the unsaturated dinitriles in the range of about 0.1:100 to about 0.6:100, a weight ratio of palladium to ruthenium in the range of about 1:1 to about 5:1, a mol ratio of ammonia to cyano groups in the range of about 7:1 to about 15:1, a hydrogen pressure in the range of about 750 to about 3000 psig, a weight ratio of the unsaturated dinitriles to the diluent in the range of about 0.1:100 to about 20:100, and a temperature in the range of about 165° C to about 225° C; wherein said at least one unsaturated dinitrile compound constitutes at least 5 weight percent of the unsaturated dinitriles in said feedstock; wherein said at least one unsaturated dinitrile compound is converted primarily to a saturated diamine having the formula

wherein R and R' are as defined hereinbefore; wherein said at least one unsaturated dinitrile reactant is converted primarily to a saturated diamine having the formula

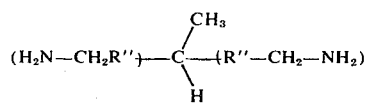

wherein R'' is as defined hereinbefore; and recovering a diamine product containing less than about 1 weight percent unsaturated diamines.

11. A process in accordance with claim 10 wherein the water constitutes from about 8 to about 16 weight percent of said diluent.

12. A process in accordance with claim 11 wherein said first catalyst component is palladium, said second catalyst component is ruthenium, and said diluent consists essentially of water and tertiary butanol.

13. A process in accordance with claim 12 wherein said feedstock comprises 5-methylene-nonanedinitrile and 5-methyl-4-nonenedinitrile.

14. A process in accordance with claim 1 further comprising recovering a diamine product containing less than about 1 weight percent unsaturated diamines.

15. A process in accordance with claim 1 further comprising recovering a diamine product essentially free of unsaturation.

16. A process for the catalytic hydrogenation of an unsaturated dinitrile feedstock comprising at least one unsaturated dinitrile compound of the formula

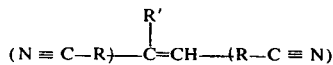

wherein each R is independently selected from the group consisting of an alkylene radical and an alkylidene radical, R' is an alkyl radical, and the number of carbon atoms in said compound is in the range of 7 to 30; which comprises contacting, at suitable hydrogenation conditions for the at least substantially complete hydrogenation of said at least one unsaturated dinitrile compound, said feedstock with ammonia; hydrogen; a diluent consisting essentially of water and at least one unsubstituted tertiary aliphatic alcohol having 4 to 12 carbon atoms per molecule, the concentration of water in the diluent being suitable to permit the desired degree of hydrogenation under said hydrogenation conditions; and a catalyst comprising a first catalyst component selected from the group consisting of elemental palladium and palladium compounds which are reducible by hydrogen to elemental palladium at said hydrogenation conditions, and mixtures thereof, and a second catalyst component selected from the group consisting of elemental ruthenium, ruthenium compounds which are reducible by hydrogen to elemental ruthenium at said hydrogenation conditions, and mixtures thereof, to thereby effect the at least substantially complete hydrogenation of said at least one unsaturated dinitrile compound to the corresponding branched-chain saturated aliphatic diamine; said suitable hydrogenation conditions comprising a weight ratio of the total of palladium and ruthenium present to the unsaturated dinitriles in the range of about 0.001:100 to about 30:100, a mol ratio of ammonia to cyano groups in the range of about 1:1 to about 25:1, a hydrogen pressure in the range of about 500 to about 5000 psig, a weight ratio of the unsaturated dinitriles to the diluent in the range of about 0.001:100 to about 25:100, a weight ratio of palladium to ruthenium in the range of about 0.1:10 to about 10:1, and a temperature in the range of about 100°C to about 300°C; and wherein the water constitutes from about 5 to about 25 weight percent of said diluent.

17. A process in accordance with claim 16 wherein the water constitutes from about 6 to about 20 weight percent of said diluent.

18. A process in accordance with claim 17 wherein said temperature is in the range of about 160°C to about 250°C.

19. A process in accordance with claim 18 wherein the water constitutes from 8 to 16 weight percent of said diluent.

20. A process in accordance with claim 19 wherein said weight ratio of the total of palladium and ruthenium present to the unsaturated dinitriles is in the range of about 0.01:100 to about 5:100.

* * * * *